(12) United States Patent
Te Baay et al.

(10) Patent No.: US 7,560,579 B2
(45) Date of Patent: Jul. 14, 2009

(54) PROCESS FOR PREPARING PURIFIED FATTY ACIDS

(75) Inventors: Franz-Josef Te Baay, Rees (DE);
Holger Riemensperger, Illertissen (DE);
Ingo Mensink, Ochtrup (DE)

(73) Assignee: Oleon N.V., Ertvelde (BE)

( * ) Notice: Subject to any disclaimer, the term of this patent is extended or adjusted under 35 U.S.C. 154(b) by 0 days.

(21) Appl. No.: 10/564,143

(22) PCT Filed: Jul. 5, 2004

(86) PCT No.: PCT/EP2004/007501

§ 371 (c)(1),
(2), (4) Date: Mar. 22, 2006

(87) PCT Pub. No.: WO2005/005584

PCT Pub. Date: Jan. 20, 2005

(65) Prior Publication Data

US 2006/0167291 A1    Jul. 27, 2006

Related U.S. Application Data

(60) Provisional application No. 60/502,936, filed on Sep. 16, 2003.

(30) Foreign Application Priority Data

Jul. 10, 2003    (EP)   ................................. 03077167

(51) Int. Cl.
*C11B 3/00*    (2006.01)
(52) U.S. Cl. ..................................................... 554/175
(58) Field of Classification Search ................. None
See application file for complete search history.

(56) References Cited

U.S. PATENT DOCUMENTS

| | | | | |
|---|---|---|---|---|
| 2,583,028 | A | 1/1952 | Terry et al. | ............... 260/398.5 |
| 2,862,943 | A | 12/1958 | Wheeler | ...................... 260/419 |
| 5,288,619 | A | 2/1994 | Brown et al. | ................. 435/134 |
| 6,147,196 | A | 11/2000 | Stern et al. | ................... 534/170 |
| 6,423,857 | B1 * | 7/2002 | Copeland et al. | ............ 554/198 |
| 6,590,113 | B1 | 7/2003 | Sleeter | ......................... 554/1 |
| 2001/0026832 | A1 | 10/2001 | Remmereit | ................. 426/630 |

FOREIGN PATENT DOCUMENTS

| | | |
|---|---|---|
| EP | 0 968 993 B1 | 1/2000 |
| WO | WO 97/24420 | 7/1997 |
| WO | WO9724420 * | 7/1997 |

OTHER PUBLICATIONS

International Search Report for International Application No. PCT/EP2004/007501, Nov. 29, 2004.
Derwent Abstract of EP 0968993.
"Ullmann's Encyclopedia of Industrial Chemistry," 6th Edition, John Wiley & Sons, Inc.; (2005) pp. 1-34.

* cited by examiner

*Primary Examiner*—Deborah D Carr
(74) *Attorney, Agent, or Firm*—Scully, scott, Murphy & Presser, P.C.

(57) ABSTRACT

The present invention relates to a process for preparing fatty acids derived from oils and/pr fats with a phosphorus content below 200 ppm in good yield and with good color and color stability, which process comprises the steps of (A) hydrolytic splitting of degummed oils and/or fats, (B) at least one thermal pre-treatment of a composition comprising crude fatty acids, and (C) high vacuum distillation of the thermally pre-treated composition comprising crude fatty acids.

22 Claims, No Drawings

PROCESS FOR PREPARING PURIFIED FATTY ACIDS

This case was file under the Patent Cooperation Treaty on Jul. 5, 2004 and claims priority of U.S. provisional application Ser. No. 60/502,936 and filed on Sep. 16, 2003 and European patent application No. 03077167.9 filed on Jul. 10, 2003.

The present invention relates to a process for preparing free fatty acids derived from oils and/or fats In good yield and with good colour quality and colour stability, which process comprises (A) a hydrolytic splitting step of a oil and/or fat, or a mixture of oils and/or fats, to give a composition comprising crude fatty acids, (B) at least one thermal pre-treatment step of the crude fatty acids obtained by step (A) to produce a thermally pre-treated composition, and (C) a high vacuum distillation step of the heat-treated composition obtained by step (B).

In the production process for the preparation of fatty acids, most often inexpensive starting materials are used, such as, natural oils or fats, or other fatty materials. The oils and/or fats are subjected to appropriate splitting conditions to release fatty acids. Examples of such splitting processes include hydrolysis by pressure splitting and enzymatic splitting. After the splitting step, the fatty acids typically contain impurities, such as, unsplit or incompletely split glycerides (like mono- and diglycerides), colour bodies, and compounds like sterols and phosphatides. In this respect, it is noted that in this description the terms "crude fatty acids" and "crude fatty acid product" refer to free fatty acids that are contaminated with one or more of the above-mentioned impurities. Furthermore, the terms "free fatty acids" and "fatty acids" relate to aliphatic monocarboxylic acids having varying degree of unsaturation and that are derivable from glycerides (the esters of glycerol with said aliphatic monocarboxylic acids). Said glycerides are widely available in nature as oils and fats. During the splitting process undesirable polymerisaton and decomposition reactions may take place, which results in additional contamination of the crude fatty acids.

The alkali hydrolysis splitting process, commonly known as saponification, is a less preferred splitting process because it has several drawbacks. One drawback is that this process requires a considerable amount of chemicals. More specifically, base (alkali) such as sodium or potassium hydroxide is used to do a full saponification of crude oils and fats in order to obtain a fatty acid salt (soap). Afterwards, an acid such as sulphuric or hydrochloric acid is needed to neutralise the reaction mixture and release the free fatty acids. The use of this base and acid makes the process economically and environmentally less viable, since an aqueous waste stream with large amounts of salts is produced during the process. A second drawback is that the saponification of crude oils and fats is often done as a batch process. Again, from an economical point of view this is not desirable.

Another splitting process makes use of a the pressure splitter wherein typically the fat or oil is introduced at one end and water introduced at the opposite end thereof in a countercurrent flow patter. Such a process is also the preferred splitting process according to the invention. In such a process, the pressure splitter provides substantial amounts of heat and pressure to the mixture of triglyceride and water to effect the hydrolysis. However, because the triglyceride is hydrophobic, the amount of actual contact between the water phase and the fat phase is relatively low. It is believed that after a period of time in the splitter individual triglyceride molecules incompletely hydrolyze, splitting off one acid molecule to create a diglyceride or two acid molecules to form a monoglyceride. The mono- and diglycerides are less hydrophobic than the starting triglyceride, and mix more thoroughly with water. As a result, the mono- and diglycerides function as emulsifiers to improve mixing of the triglyceride with water. Under the turbulent conditions within the pressure splitter, it is believed that the mono- and diglycerides improve the extent of mixing between the triglyceride and water, thereby facilitating the hydrolysis reaction.

The crude fatty acid product obtained by pressure splitting fats and oils typically comprises about 95-99% by weight (wt %) of free fatty acids, based on the weight of the crude fatty acid product and about 1-5 wt % of impurities, such as the above-mentioned unsplit glycerides, colour bodies, sterols, phosphatides, but also minor amounts of water and other compounds may be present.

For the purification of crude fatty acids, several methods have been developed over the years. Distillation and/or fractionation are presently the most important of these (thermal) purification methods. Nowadays, many different distillation and/or fractionation processes are available, each process describing specific reaction conditions with respect to, for example, temperature and pressure, and each process specifically fine-tuned to provide pure fatty acids in good yield and with specific properties, for example, good colour quality and/or good colour stability.

It is noted that the oil and/or fat used as feed for the present process is a crude or degummed oil and/or fat, or mixture of oils and fats with a phosphorus content below 200 mg/kg (<200 ppm). Degumming is a refining step of oils and fats performed to remove undesired phosphor-containing species (phosphatides). Conventional degumming is by steam, enzymatic or chemical treatment to remove non-hydratable phosphatides. Typically, the phosphorus level of degummed oils ranges between 10 and 200 mg/kg. The crude or degummed oil and/or fat typically still contains from 0.2-3% impurities. Preferably, the amount of phospholipids in the crude or degummed oils and/or fats for use in the present invention is below 1%, more preferably below 0.8% and most preferably, below 0.6% by weight, based on the total weight of the crude or degummed oils and/or fats.

Further refining steps can be applied to the oil and/or fat such as neutralisation, bleaching, winterization which are commonly used during oil refining to further remove the amount of impurities. These additional steps are less desirable as they increase the total costs of the present process.

U.S. Pat. No. 2,862,943 describes a process for the purification of crude fatty acids to obtain fatty acids with improved colour. A small amount of boric acid compound is mixed with the crude fatty acids at the time of distillation. In some instances the crude fatty acid mixture is treated for a period of time at elevated temperatures of 100-300° C. in the presence of the boric acid prior to the distillation. Thereafter, the crude fatty acid product is distilled at 0.667 kPa to give purified fatty acids. The process of U.S. Pat. No. 2,862,943 requires the use of boric acid to achieve the objective and is therefore economically less profitable for industry.

EP 0,968,993 discloses a process for treating natural fatty acids before their subsequent distillation, wherein the fatty acids are heated to a temperature of 150-230° C. and hydrogen peroxide is introduced in an amount of 0.5-5%, based on the amount of crude fatty acid to be treated. After completion of the hydrogen peroxide introduction, a secondary reaction takes place at the same temperature for at least 10 minutes, the chromophores present in the crude fatty acids are converted to higher molecular weight substances, which remain in the residue in the subsequent distillation at 1 kPa. The use of hydrogen peroxide in the process of EP 0,968,993 makes the process economically less viable.

Finally, in U.S. Pat. No. 2,583,028 a process is disclosed to improve the colour and colour stability of saturated higher fatty acids by treatment with a small quantity of $BF_3$ at a temperature of 70-200° C. for a period of 2-4 hours. Thereafter, the fatty acid products are distilled in vacuo in order to give a purified fatty acid product. The process of U.S. Pat. No. 2,583,028 requires the use of $BF_3$, which makes the process economically less profitable.

It is further noted that WO 97/24420 does not relate to a process wherein degummed fats and oils are used. On the contrary, herein a sterol and phospholipids-rich feed of lipids is used. In the process of WO 97/24420, this crude lipid feed is first hydrolysed by the addition of base or acid, to give a crude fatty acid product that is contaminated with, inter alia, sterols, unreacted phospholipids and hydrolysed phospholipids. Due to the phospholipids and the formation of sterol esters a substantial amount of fatty acid is lost and alcohols are to be used for separation purposes. Therefore, the process of WO 97/24420 is economically not feasible for the industrial preparation of common fatty acids. Furthermore, not only the yield on fatty acids is low, it also involves steps that are conducted in a batch-wise fashion, and furthermore requires a saponification splitting step. The saponification step requires the use of additional chemicals, but is needed because a high pressure splitting process would result in polymerization of the long chain poly unsaturated fatty acids used in WO 97/24420. There is no suggestion of an economical process to make fatty acids which are low in colour and colour stable.

A problem that is still unresolved by the prior art processes is to provide an economically feasible process to produce free fatty acids, or mixtures of free fatty acids, with good colour quality and colour stability in good yield. It is noted that the term "colour quality" refers to the colour just after distillation of the crude fatty acid product, whereas the term "colour stability" relates to the colour of the free fatty acids when measured after storage for 21 days at 45° C. under normal atmospheric conditions.

Hence, it is an objective of the present invention to provide a process overcoming this problem, said process being pre-eminently suited for preparing purified fatty acids in an economically attractive way and to produce free fatty acids with the above mentioned properties in good yield.

We have now found that such free fatty acids, or mixture of free fatty acids, can be obtained if the process comprises (A) a hydrolytic splitting step of oils and/or fats with a phosphorous content below 200 ppm to give a composition comprising crude fatty acids and monoglycerides, (B) at least a thermal pre-treatment step of the composition obtained by step (A), and (C) distillation in a high vacuum distillation unit of pre-treated composition obtained by step (B), wherein the composition that is obtained in the thermal pre-treatment step comprises a lower amount of monoglycerides compared to the amount of monoglycerides in the crude fatty acids obtained by step (A) and is preferably below 0.5% by weight (wt %) of monoglycerides, more preferably below 0.25 wt % of monoglycerides, even more preferably below 0.1 wt % of monoglycerides, and most preferably below 0.05 wt % of monoglycerides, based on the weight of thermally pre-treated composition, with the proviso that the hydrolytic splitting step (A) is not a saponification step, because of the drawbacks mentioned before. Preferably, the product obtained by step (C) comprises below 0.5% by weight (wt %) of monoglycerides, based on the weight of product after distillation and has a colour quality characterised by a Lovibond Red (Lr) (5¼) value below 0.6, preferably below 0.4 and a Lovibond Yellow (Ly) (5¼) value below 5.5, preferably below 4.0, and a colour stability of Lr (5¼) below 2.0, preferably below 1.8 and Ly (5¼) below 24, preferably below 20. The Lovibond color values are determined in the conventional way using a Lovibond Tintometer® using a cell length of 5 and a quarter inch.

Accordingly, we claim a process for preparing one or more purified fatty acids with good colour quality and colour stability, said process comprising at least the steps of:
(A) hydrolytic splitting of one or more oils and/or fats with a phosphorous content below 200 ppm and separating a composition comprising crude fatty acids,
(B) heat-treating the composition obtained by step (A) in a thermal pre-treatment unit to reduce the amount of monoglycerides, and
(C) distilling the heat-treated composition obtained by step (B) in a high vacuum distillation unit, the distillate being the desired purified fatty acid, wherein the composition that is obtained by the thermal pre-treatment step (B) comprises a lower amount of monoglycerides compared to the amount of monoglycerides in the crude fatty acids obtained by step (A) and is preferably below 0.5% by weight (wt %) of monoglycerides, more preferably below 0.25 wt % of monoglycerides, even more preferably below 0.1 wt % of monoglycerides, and most preferably from 0 to below 0.05 wt % of monoglycerides, based on the weight of thermally pre-treated composition, with the proviso that the hydrolytic splitting step (A) is not a saponification step.

Processes according to the present invention may be a batch, semi-batch, or continuous processes. From an economic point of view, it is preferred to have only continuous processes.

The process of the invention is extremely suitable for making pure fatty acids from oils and/or fats of technical purity (phosphorous content below 200 ppm and at least 80%, preferably at least 90%, most preferably at least 95% by weight of glycerides). In that case, a yield of at least 90%, preferably at least 92%, most preferably at least 95%, all on a molar basis, of the fatty acid portion in the glyceride is retrieved in the form of a pure fatty acid. Depending on the oils and/or fats that are used as the feed, a variety of mixtures of one or more fatty acids can be produced with the process according to the invention. In a preferred process according to the invention, the composition of the fatty acids (i.e. the various types and amounts of fatty acids) resulting from the distillation step equals the composition of the fatty acid fraction of the glycerides that were splitted. Furthermore, the present process allows the production of methyl ester-free products, meaning that the level of fatty acid methyl esters in the distilled product is below 0.1% by weight. For this reason, a preferred embodiment of the invention relates to purified fatty acids produced in accordance with the invention, that are characterized by containing more than 99% by weight of fatty acid. More preferred fatty acids also contain less than 0.05% by weight of each of mono-, di-, and triglycerides and have a Lovibond (5¼) red and yellow value of below 1 and 4, respectively and a Lovibond (5¼) red and yellow colour stability of below 2 and 20, respectively.

In a preferred embodiment of the present invention at least part of the residue that is obtained by the distillation step (C) is recycled to step (A) before the hydrolysis step. If so desired, the residue can be combined with the oils and/or fats of the feed.

In another preferred embodiment of the present invention, the composition that is obtained by the thermal pre-treatment step (B) comprises at least 80% by weight (wt %) of free fatty acids, preferably at least 85 wt % of free fatty acids, more preferably at least 90 wt % of free fatty acids, and most preferably at least 92 wt % of free fatty acids, based on the weight of the thermally pre-treated composition.

Suitable oils and fats that are preferably used in step (A) of the present process are selected from the group comprising of crude or refined vegetable oils and fats, crude or refined animal fats and oils, and acid oils with a total phosphorous amount of below 200 ppm. More preferred is the use of degummed vegetable oils and fats, and most preferred is the use of degummed vegetable oils and fats that, after hydrolytic splitting of said oils and fats, provide saturated or unsaturated, optionally hydroxy containing, crude fatty acids with 6 to 24 carbon atoms, or mixtures thereof. Examples of particularly preferred vegetable oils and fats include oils selected from coconut oil, palm oil, palmkernel oil, sunflower oil, soybean oil, rapeseed oil, high erucic rapeseed oil, castor oil, linseed oil, safflower oil, corn oil, cottonseed oil, groundnut oil, and canola oil. Also a mixture of one or more oils and one or more fats can be used in the present process.

Suitable hydrolytic splitting processes to release crude fatty acids from oils and fats are conventional splitting processes, such as, thermal high pressure splitting and enzymatic splitting, which are extensively described in the art and are well-known to a man skilled in the art and are, for instance, presented in Ullmann's Encyclopedia of Industrial Chemistry, 6$^{th}$ Edition, John Wiley & Sons, Inc. Preferably, no separating aids, such as, alcohols are used to facilitate the formation of distinct crude fatty acids and aqueous phases. The composition that is used in step B of the present process is the distinct crude fatty acid phase of this splitting process. Preferably, said crude fatty acid phase that is used in step B is essentially glycerol-free, meaning that free glycerol levels in the crude fatty acid are preferably below 1% by weight, more preferably below 0.5% by weight and most preferably below 0.1% by weight. In another preferred embodiment, the splitting degree of the fatty acids after step A, measured as the acid value (mg KOH needed to neutralize one gram of the crude fatty acid, is at least 150, preferably at least 170 and more preferably at least 180 mg KOH/g. For economic and environmental reasons as explained above in more detail, the use of saponification as hydrolytic splitting technique is excluded from this invention.

It is noted that for commercial products that are produced on large scale, it is important that these products can be prepared in a cost efficient way and that the quality properties are suitable for the various industrial applications. For fatty acids, this means that yield and colour and colour stability are important properties. As described above, crude fatty acids derived by hydrolytic splitting of oils and fats often contain impurities like unsplit and incompletely-split glycerides, substances like sterols and residual phosphatides, colour bodies, and polymerisation and decomposition products. Colour and colour stability of fatty acids are influenced by the presence of, inter alia, monoglycerides and other colour bodies. An additional drawback of the presence of monoglycerides is that these compounds may harm the application performance of the final fatty acid product. Consequently, it is highly preferred to produce purified fatty acids that are essentially monoglyceride free. With the term "essentially free" is meant here that the amount of monoglycerides is such that any remaining amount of monoglyceride does not harm the colour quality and colour stability of the fatty acid product, nor the application performance of the final fatty acid product. The final fatty acid product, i.e. free fatty acids that are obtained after distillation step (C), preferably comprises below 0.5% by weight (wt %) of monoglycerides, more preferably below 0.25 wt %, even more preferably below 0.1 wt % of monoglycerides, and most preferably from 0 to below 0.05 wt %, based on the weight of the final fatty acid product.

During the thermal pre-treatment step (B), several reactions may take place. According to the present invention, monoglycerides that are present in the composition obtained by step (A) are reesterified under the thermal pre-treatment conditions to form higher boiling compounds, mainly di- and triglycerides. These di- and triglycerides remain in the residue during the subsequent distillation step (C). Because of the reesterification of monoglycerides, the crude fatty acid-containing composition that is obtained after the thermal pre-treatment step comprises a lower amount of monoglycerides compared to the amount of monoglycerides in the composition obtained by step (A). The thermal pre-treatment step (B) of the present invention provides a thermally pre-treated composition comprising an amount of preferably below 0.5% by weight (wt %) of monoglycerides, more preferably below 0.25 wt % of monoglycerides, even more preferably below 0.1 wt % of monoglycerides, and most preferably below 0.05 wt % of monoglycerides, based on the weight of thermally pre-treated composition. Furthermore, in addition to a reduced amount of monoglycerides obtained by step (B), it is advantageous if the thermally pre-treated composition comprises a high amount of free fatty acids. Particularly advantageous is a thermally pre-treated composition comprising at least 80% by weight (wt %) of free fatty acids, preferably at least 85 wt % of free fatty acids, more preferably at least 90 wt % of free fatty acids, and most preferably at least 93 wt % of free fatty acids, based on the weight of the thermally pre-treated composition. Since monoglycerides have a substantial influence on the performance, as well as the colour quality and colour stability of the final fatty acid product, the reesterification of these monoglycerides during the thermal pre-treatment step is a very effective and desirable reaction. Additional reactions that may also take place during the thermal pre-treatment step are the polymerisation and/or decomposition reactions of (reactive) coloured bodies. Decomposed coloured bodies can be collected as separate fractions during the subsequent distillation step, whereas polymerised coloured bodies remain in the residue after distillation. The present process comprises at least one thermal pre-treatment step, although it also possible to carry out this thermal pre-treatment step more than once. It is preferred to do just one thermal pre-treatment step.

The thermal treatment step (B) can be conducted in a thermal pre-treatment unit that is working in a batch, semi-batch, or continuous fashion. The thermal pre-treatment step may be conducted at a temperature in the range of 150-280° C., more preferably at a temperature of 200-250° C., and most preferably at a temperature of about 225° C. If the residence time of the crude fatty acids in the thermal pre-treatment unit is too long, undesirable reactions may occur which disadvantageously affect the overall yield of the present process. On the other hand, if the residence time of the crude fatty acid In the thermal pre-treatment unit is too short, impurities may remain in the final fatty acid product that can have a detrimental influence on the colour quality and colour stability of the final fatty acid product.

For economic feasibility of the overall process, it is particularly preferred that the thermal pre-treatment unit in step (B) is a continuously working unit. The reaction conditions in this thermal pre-treatment unit are such that the composition obtained by step (A) that is going through this continuously working unit has a narrow residence time distribution. The residence time distribution $\phi$ is a dimensionless number that for a conventional stirred tank reactor generally varies between 0.2 and 6.0 ($\phi=t/t'$, wherein t is the actual residence time of a component (of a composition) and t' is the average residence time of all components (of a composition)). Typically, for a narrow residence time distribution, $\phi$ is at least 0.7-1.5 and in the most preferred situation each of these numbers approximate to 1. It is noted that only in the case of a batch process the residence time distribution $\phi$ is 1. For batch, semi-batch, and continuous thermal pre-treatments applies that the average residence time associated with the temperature at which the thermal pre-treatment is preferably carried out varies from approximately 10 minutes to 6 hours. At a temperature of 150° C. the average residence time is approximately 6 hours and at a temperature of 280° C. the average residence time is approximately 10 minutes. At the most preferred temperature of about 225° C., the average residence time is approximately 1 hour.

Preferably, the process of the present invention does not include a washing and subsequent drying step between the thermal pre-treatment step (B) and the distillation step (C).

The high vacuum distillation step (C) of the present invention is based on a high vacuum distillation method, for example, thin film evaporation, (centrifugal) molecular distillation, wiped film distillation, or falling film distillation. Each of these distillation technologies allows the use of very low pressure (high vacuum) during the distillation process of below 1 kPa. For the present distillation process, preferably a pressure of 0.5-0.001 kPa and a temperature of 100-200° C. are applied for the distillation of the thermally pre-treated composition. More preferably, a pressure of 0.1-0.001 kPa and a temperature of 120-180° C. are applied. Preferably, the high vacuum distillation step (C) is. based on thin film evaporation. The principle of thin film evaporation in the process of the present invention is that thermally pre-treated composition is heated in a device that is suitable to form a thin film of the composition material, which can be achieved, for example, by rotating the device or by applying a rotating wiper system. The formation of a thin film allows a gentle and steady evaporation of the various components that are present in the thermally pre-treated composition. Because a thin film allows quick evaporation, the residence time of the components of the composition in the heated device is short. This short residence time prevents the occurrence of undesirable polymerisation and decomposition reactions. A particularly preferred thin film distillation method is short path distillation. In a short path distillation unit, the distance between the evaporation area and the condensing area is much shorter compared to conventional distillation units.

In one embodiment of the present invention, at least part of the residue of the distillation step (C) is recirculated to step (A). Residue that is recirculated to step (A) is either admixed with newly added oils and/or fats prior to or during the hydrolytic splitting process or collected separately and recycled without admixing with newly added oils and/or fats. Although the residue may be continuously recirculated, It will be obvious that after some recycle loops the residue is contaminated with undesired components to such an extent that it is more desirable to discard the residue. Alternatively, part of the recycle may be bled off to get a constant level of contaminants In the process.

Optionally, one or more conventional additives that are advantageous for the removal of coloured bodies may be used in a step before the distillation step C of the present process. These additives may be added to and admixed with the fatty acid containing composition In varying concentrations after step (A) and before, during, or after the thermal pre-treatment step (B). If so desired, the colour bodies can be removed in a separate treatment step before the distillation step (C). The use of one or more additives during distillation step (C) is undesired since such a use is not effective because the fatty acid and the additives have insufficient time to interact. Examples of suitable additives include, but are not limited to, phosphoric acid, hydrogen peroxide, sulphuric acid, boric acid, and mixtures thereof. If such additives are used, they are typically used in very low amounts. More specifically, boric acid is to be used in an amount less than 0.1%, preferably less than 0.05%, boron trifluoride ($BF_3$) in an amount less than 0.5%., preferably less than 0.1%, and hydrogen peroxide ($H_2O_2$) in an amount less than 5%, preferably less than 2%, all based on the amount of crude fatty acid to be treated.

The presence of mono-, di-, and/or triglycerides and possible other components in a composition comprising free fatty acids may be determined by conventional Gas Chromatography (GC) methods, or Gel Permeation Chromatography (GPC) techniques, prior, during, or after any of the steps of the present process. GPC is a high performance liquid chromatography technique for the separation of components based on their molecular size in solution. GPC separates the sample into its discrete components and determines the molecular weight distribution of a sample.

In order to further elucidate the present invention, the following examples are given as an illustration:

High Pressure Splitting (HPS)

About 200 tons (t) of degummed linseed oil is split in a commercial continuous countercurrent splitter at 230° C. and 33 bar (with a feed rate of 4.5 t/h). The oil is introduced from the bottom, water from the top. Difference in densities combined with the pumping force with which degummed linseed oil is introduced to the countercurrent splitter causes mixing of the oily and aqueous currents. The crude fatty acids (i.e. split oil product comprising free fatty acids, mono-, di-, and triglycerides) that are obtained are isolated from the aqueous waste stream comprising glycerol, collected and analysed (Table 1). Optionally, part of the isolated and collected crude fatty acids may be recirculated to the countercurrent splitter and admixed with newly added crude linseed oil at the bottom of the splitter, which will reduce the induction phase of the splitting process.

TABLE 1

| Components analysed by GPC | Degummed linseed oil (wt %)[1] | High pressure splitting Crude fatty acids (wt %)[2] |
|---|---|---|
| Monomer (FFA)[3] content | <3[4] | 89.4 |
| Monoglyceride content | | 2.8 |
| Diglyceride content | | 6.9 |
| Triglyceride content | >97[4] | 0.9 |

[1]Weight percent, based on the total amount of degummed crude linseed oil.
[2]Weight percent, based on the total amount of crude fatty acid after splitting.
[3]FFA = Free fatty acid
[4]Typical amount in a composition of naturally occurring crude linseed oil

COMPARATIVE EXAMPLE A

The crude fatty acids obtained from degummed linseed oil In the high pressure splitting as described above, were distilled in a conventional continuous distillation plant at 270° C. and 0.5 kPa (with a feed rate of 4.3 t/h) as described in "Ed. R. W. Johnson, E. Fritz; Fatty Acids in Industry: Processes, properties, derivatives, applications; Marcel Dekker, Inc., New York, 1989". The yield was 83% of distilled product, based on the amount of crude fatty acids that was distilled. Analysis of the residue Indicated an amount of polymerised fatty acids of 10.3% as determined by GPC, based on the amount of residue. For analytical data see Table 2. About 50 t of residue that was obtained by this distillation was again subjected to the conditions of high pressure splitting as described above and subsequently the crude fatty acids that were obtained by this splitting step were again subjected to the conventional continuous distillation conditions, to give a second amount of free fatty acids in about 50% yield.

TABLE 2

| Components analysed by GPC | Crude fatty acids by HPS (wt %) | Comparative Example A | |
|---|---|---|---|
| | | Product after dist. (wt %)[1] | Product after 2nd dist. (wt %)[2] |
| Monomer (FFA) content | 89.4 | ~100 | ~100 |
| Monoglyceride content | 2.8 | n.d.[7] | n.d.[7] |
| Diglyceride content | 6.9 | n.d.[7] | n.d.[7] |
| Triglyceride content | 0.9 | n.d.[7] | n.d.[7] |
| Colour quality[3] | | | |
| Lr (5¼)[5] | | 0.6 | 0.8 |
| Ly (5¼)[6] | | 5.5 | 7.8 |
| Colour stability[4] | | | |
| Lr (5¼)[5] | | 1.9 | — |
| Ly (5¼)[6] | | 24 | — |

[1] Weight percent, based on the total amount of product after distillation
[2] Product after high pressure splitting of the residue of the first distillation and subsequent second distillation. Weight percent, based on the total amount of product after distillation
[3] Fresh colour after distillation
[4] Colour after 21 days storage at 45° C.
[5] Lr (5¼) is Lovibond Red measured in a 5¼ inch cell
[6] Ly (5¼) is Lovibond Yellow measured in a 5¼ inch cell
[7] Not detectable (n.d.), i.e. <0.05% of weight, based on the amount of product after distillation

COMPARATIVE EXAMPLES B AND C

The crude linseed oil-derived fatty acids obtained by the high pressure splitting above were distilled in a short path distillation unit at 150° C. (Comparative Example B) or 175° C. (Comparative Example C) and 0.002 kPa (with a feed of 400 kg/h) in both Comparative Examples. The yields are 81% and 88% of distilled product, based on the amount of crude fatty acids that was distilled, for Comparative Example B and Comparative Example C, respectively. For the analytical data see table 3.

TABLE 3

| Components analyzed by GPC | Crude fatty acids by HPS (wt %) | Comp. Example B Product after dist. with SPD[1] at 150° C. (wt %)[2] | Comp. Example C Product after dist. with SPD[1] at 175° C. (wt %)[2] |
|---|---|---|---|
| Monomer (FFA) content | 89.4 | 98.5 | 97.5 |
| Monoglyceride content | 2.8 | 1.5 | 2.5 |
| Diglyceride content | 6.9 | n.d.[7] | n.d.[7] |
| Triglyceride content | 0.9 | n.d.[7] | n.d.[7] |
| Colour quality[3] | | | |
| Lr (5¼)[5] | | 0.5 | 0.9 |
| Ly (5¼)[6] | | 4.5 | 7.2 |
| Colour stability[4] | | | |
| Lr (5¼)[5] | | 3.2 | 5.2 |
| Ly (5¼)[6] | | 36 | 52 |

[1] SPD = Short Path Distillation
[2] Weight percent, based on the total amount of product after distillation.
[3] Fresh colour after distillation
[4] Colour after 21 days storage at 45° C.
[5] Lr (5¼) is Lovibond Red measured in a 5¼ inch cell
[6] Ly (5¼) is Lovibond Yellow measured in a 5¼ inch cell
[7] Not detectable (n.d.), i.e. <0.05% of weight, based on the amount of product after distillation Example 1

The crude linseed oil-fatty acids obtained by the high pressure splitting above were pre-treated in a batch reactor by reesterification of the glycerides in the crude fatty acids at 220° C. for 1 h at 2 kPa. Next, the pre-treated crude fatty acid product was distilled in a short path distillation unit at 150° C. at 0.001 kPa (with a feed rate of 15.5 kg/h). The yield of distilled product after batch thermal pre-treatment and short path distillation was 83%. Analysis of the residue of the distillation indicated an amount of polymerised fatty acids of 4.7% as determined by GPC, based on the amount of residue. For the analytical data see table 4.

TABLE 4

| Components analyzed by GPC | Crude fatty acids by HPS (wt %) | Example 1 | |
|---|---|---|---|
| | | Product after pre-treatment of crude fatty acids (wt %)[1] | Product after pre-treatment and dist. (wt %)[2] |
| Monomer (FFA) content | 89.4 | 84.0 | 100 |
| Monoglyceride content | 2.8 | n.d.[7] | n.d.[7] |
| Diglyceride content | 6.9 | 8.2 | n.d.[7] |
| Triglyceride content | 0.9 | 7.8 | n.d.[7] |
| Colour quality[3] | | | |
| Lr (5¼)[5] | | | 0.1 |
| Ly (5¼)[6] | | | 1.8 |
| Colour stability[4] | | | |
| Lr (5¼)[5] | | | 0.7 |
| Ly (5¼)[6] | | | 12 |

[1] Weight percent, based on the amount of crude fatty acids after pre-treatment.
[2] Weight percent, based on pre-treated crude fatty acids after distillation.
[3] Fresh colour after distillation
[4] Colour after 21 days storage at 45° C.
[5] Lr (5¼) is Lovibond Red measured in a 5¼ inch cell
[6] Ly (5¼) is Lovibond Yellow measured in a 5¼ inch cell
[7] Not detectable (n.d.), i.e. <0.05% of weight, based on the amount of product after distillation Example 2

The crude linseed oil-based fatty acids obtained by the high pressure splitting above were continuously fed at a specific rate $R_1$ (feed rate $R_1$ of 0.2 L/h) into a stirred 2 L glass reactor filled with 1.2 L of crude fatty acids at 200° C. At the same rate $R_1$ as product was fed Into the reactor, an amount of product was removed from the reactor and then cooled to 30° C. In a heat exchanger. The rate $R_1$ was such that an average residence time of 360 minutes In the reactor was achieved. The cooled product was collected, analysed, and subsequently distilled in a short path distillation unit at 150° C. and 0.001 kPa (feed rate $R_2$ of 0.6 kg/h). The yield of distilled product was 84%. Analysis of the residue of the distillation indicated an amount of polymerised fatty acids of 5.9% as determined by GPC, based on the amount of residue. The analytical data are presented in Table 5. The residue was subjected three times to high pressure splitting conditions in a batch autoclave at 220° C. for 2 h each using an oil/water ratio of 1:1. The total amount of crude fatty acids that were obtained after these three treatments were then thermally pre-treated at 200° C. for 1 h. Finally, distillation of the thermally pretreated crude fatty acids as described in Example 2 afforded free fatty acids in about 70% yield. Therefore the total yield can be calculated to be 84%+0.70*16%=95%.

TABLE 5

| | | Example 2 | |
|---|---|---|---|
| Components analyzed by GPC | Crude fatty acids by HPS (wt %) | Product after pre-treatment of crude fatty acids (wt %)[1] | Product after pre-treatment and dist. (wt %)[2] |
| Monomer (FFA) content | 89.4 | 85.8 | 100 |
| Monoglyceride content | 2.8 | n.d.[7] | n.d.[7] |
| Diglyceride content | 6.9 | 9.3 | n.d.[7] |
| Triglyceride content | 0.9 | 4.8 | n.d.[7] |
| Colour quality[3] | | | |
| Lr (5¼)[5] | | | 0.3 |
| Ly (5¼)[6] | | | 3.6 |
| Colour stability[4] | | | |
| Lr (5¼)[5] | | | 1.8 |
| Ly (5¼)[6] | | | 16 |

[1]Weight percent, based on the amount of crude fatty acids after pre-treatment.
[2]Weight percent, based on the amount of pre-treated crude fatty acids after distillation.
[3]Fresh colour after distillation
[4]Colour after 21 days storage at 45° C.
[5]Lr (5¼) is Lovibond Red measured in a 5¼ inch cell
[6]Ly (5¼) is Lovibond Yellow measured in a 5¼ inch cell
[7]Not detectable (n.d.), i.e. <0.05% of weight, based on the amount of product after distillation Examples 3-5

Example 1 was repeated using a crude soybean fatty acid (Example 3), a crude sunflower fatty acid (Example 4), and a crude rapeseed fatty acid (Example 5). The crude fatty acids were obtained by hydrolytic splitting of the corresponding degummed oils and the crude fatty acid compositions equalled the composition of the fatty acid fraction in the glyceride. Overall yields on fatty acid were more than 90% on a molar basis (basis on the moles of fatty acid fraction in the glyceride). In all cases a preferred purified fatty acid according to the invention was obtained.

From these results it is clear that the process of the present invention provides free fatty acids in good yield and with good colour quality and colour stability.

The invention claimed is:

1. A process for preparing one or more purified fatty acids, said process consisting essentially of:
   (A) hydrolytic splitting of one or more oils and/or fats with a phosphorus content below 200 ppm and separating a composition comprising crude fatty acids,
   (B) heat-treating the composition obtained by step (A) in a thermal pre-treatment unit to provide a composition of crude fatty acids comprising at least 80% by weight (wt %) of free fatty acids, and
   (C) distilling the heat-treated composition obtained by step (B) in a high vacuum distillation unit to obtain a composition of purified fatty acids comprising below 0.5% by weight of monoglyceride, wherein the composition that is obtained by the thermal pre-treatment step (B) comprises less monoglycerides than the crude fatty acids obtained by step (A), and with the proviso that the hydrolytic splitting step (A) is not a saponification step.

2. The process of claim 1 wherein the heat-treatment in step (B) is conducted at a temperature of 150-280° C.

3. The process of claim 1 wherein in step (B) the composition is heat-treated in a continuously running thermal pre-treatment unit.

4. The process of claim 3 wherein both the heat-treating and the distillation step are conducted in a continuous fashion.

5. The process of claim 1 wherein the crude fatty acids that are obtained by the thermal pre-treatment step (B) are essentially free of glycerol and have an acid value of at least 150 mg/kg KOH.

6. The process of claim 1 wherein in step (C) the heat-treated composition of step (B) is distilled at a pressure within a range of 0.5-0.001 kPa and at a temperature of from 100 to 200° C.

7. The process of claim 1 wherein step (C) is conducted in a short path distillation unit.

8. The process of claim 1 wherein at least part of the residue that is obtained by the distillation step (C) is recycled to step (A).

9. The process of claim 1 wherein the oils and/or fats with a phosphorus content below 200 ppm that are subjected to the hydrolytic splitting in step (A) are selected from the group consisting of crude or degummed vegetable oils and fats, crude or degummed animal oils and fats, and acid oils, or mixtures thereof.

10. The process of claim 1 wherein one or more additives are used before, during, or after the thermal pre-treatment step (B), but in any case after the hydrolytic splitting step (A) and prior to the distillation step (C), said additives being effective for the removal of color bodies.

11. The process of claim 2 wherein the heat-treatment in step (B) is conducted at a temperature of 200-250° C.

12. The process of claim 11 wherein the heat-treatment in step (B) is conducted at a temperature of about 225° C.

13. The process of claim 3 wherein in Step (B) the composition is heat-treated in a continuously running thermal pre-treatment unit wherein the components of the composition have a residence time distribution of 0.7-1.5.

14. The process of claim 3 wherein the heat-treating step, the distillation step and the splitting process are conducted in a continuous fashion.

15. The process of claim 1 wherein said composition of crude fatty acids comprises at least 85% by weight (wt %) of free fatty acids.

16. The process of claim 1 wherein said composition of crude fatty acids comprises at least 90% by weight (wt %) of free fatty acids.

17. The process of claim 1 wherein said composition of crude fatty acids comprises at least 93% by weight (wt %) of free fatty acids.

18. The process of claim 1 wherein in step (C) the heat-treated composition of step (B) is distilled at a pressure in the range of 0.1 to 0.001 kPa and a temperature of from 120 to 180° C.

19. The process of claim 9 wherein the oils and/or fats with a phosphorus content below 200 ppm that are subjected to the hydrolytic splitting in step (A) are selected from selected from crude or degummed vegetable oils and fats, or mixtures thereof.

20. The process of claim 9 wherein the oils and/or fats with a phosphorus content below 200 ppm that are subjected to the hydrolytic splitting in step (A) are selected from selected from crude or degummed vegetable oils and fats that, after hydrolytic splitting of said oils and/or fats, provide saturated or unsaturated, optionally hydroxy containing, crude fatty acids with 6 to 24 carbon atoms, or mixtures thereof.

21. The process of claim 1 wherein in step (C) the heat-treated composition of step (B) is distilled at a pressure within the range of 0.1 to 0.001 kPa and at a temperature of from 120 to 180° C.

22. A process for preparing one or more purified fatty acids, said process consisting essentially of:
(A) hydrolytic splitting of one or more oils and/or fats with a phosphorus content below 200 ppm and separating a composition comprising crude fatty acids,
(B) heat-treating the composition obtained by step (A) in a thermal pre-treatment unit to provide a composition of crude fatty acids comprising at least 80% by weight (wt%) of free fatty acids, and
(C) distilling the heat-treated composition obtained by step (B) in a high vacuum distillation unit to obtain a composition of purified fatty acids comprising below 0.5% by weight of monoglyceride,
wherein the composition that is obtained by the thermal pre-treatment step (B) comprises less monoglycerides than the crude fatty acids obtained by step (A), and with the proviso that the hydrolytic splitting step (A) is not a saponification step, and wherein one or more additives are used before, during, or after the thermal pre-treatment step (B), but in any case after the hydrolytic splitting step (A) and prior to the distillation step (C), said additives being effective for the removal of color bodies.

\* \* \* \* \*